US008585645B2

(12) United States Patent
Barry et al.

(10) Patent No.: US 8,585,645 B2
(45) Date of Patent: Nov. 19, 2013

(54) TREATMENT WITH HIGH TEMPERATURE VAPOR

(75) Inventors: Robert Barry, Kirkland, WA (US);
Dean Corcoran, Bothell, WA (US);
Brian Cran, Seattle, WA (US); Michael Hoey, Shoreview, MN (US); Sheldon Lee, Seattle, WA (US); Peter Lyons, Portland, OR (US)

(73) Assignee: Uptake Medical Corp., Tustin, CA (US)

( * ) Notice: Subject to any disclaimer, the term of this patent is extended or adjusted under 35 U.S.C. 154(b) by 1891 days.

(21) Appl. No.: 11/598,362

(22) Filed: Nov. 13, 2006

(65) Prior Publication Data

US 2008/0110457 A1    May 15, 2008

(51) Int. Cl.
    *A61F 7/12*    (2006.01)
(52) U.S. Cl.
    USPC ............ 604/113; 604/96.01; 604/97.01; 604/102.01; 604/102.02; 604/102.03
(58) Field of Classification Search
    USPC .......... 604/104–109, 96.01–103.14; 606/194, 606/192, 200
    See application file for complete search history.

(56) References Cited

U.S. PATENT DOCUMENTS

| 3,880,168 | A | * | 4/1975 | Berman | 128/207.15 |
|---|---|---|---|---|---|
| 4,773,410 | A | * | 9/1988 | Blackmer et al. | 128/203.26 |
| 4,915,113 | A | | 4/1990 | Holman | |
| 5,006,119 | A | * | 4/1991 | Acker et al. | 606/27 |
| 5,158,536 | A | | 10/1992 | Sekins et al. | |
| 5,331,947 | A | * | 7/1994 | Shturman | 600/115 |
| 5,503,638 | A | | 4/1996 | Cooper et al. | |
| 5,549,628 | A | | 8/1996 | Cooper et al. | |
| 5,562,608 | A | * | 10/1996 | Sekins et al. | 604/20 |
| 5,575,803 | A | | 11/1996 | Cooper et al. | |
| 5,620,440 | A | | 4/1997 | Heckele et al. | |
| 5,707,352 | A | * | 1/1998 | Sekins et al. | 604/509 |
| 5,752,965 | A | | 5/1998 | Francis et al. | |

(Continued)

FOREIGN PATENT DOCUMENTS

WO    WO 00/11927 A2    3/2000
WO    WO 02/069821 A1    9/2002

(Continued)

OTHER PUBLICATIONS

Coda, et al., "Effects of pulmonary reventilation on gas exchange after cryolytic disobstruction of endobronchial tumors," Minerva Medical, vol. 72, pp. 1627-1631, Jun. 1981 (w/ Eng. Trans.).

(Continued)

*Primary Examiner* — Kevin C Sirmons
*Assistant Examiner* — Edelmira Bosques
(74) *Attorney, Agent, or Firm* — Shay Glenn LLP

(57) ABSTRACT

Methods are describe for treating intraluminal locations such as in a patient's lung. The device is a catheter which has an elongated shaft with an inner lumen, preferably defined by an inner tubular member, formed of heat resistant polymeric materials such as polyimide and high temperature vapor is directed through the inner lumen into the intraluminal location to treat tissue at and/or distal to the location. The outer surface of the catheter is also formed of heat resistant material. An enlarged or enlargeable member, such as a balloon, is provided on a distal portion of the catheter shaft to prevent proximal flow of the high temperature vapor upon discharge from the catheter.

17 Claims, 6 Drawing Sheets

(56) References Cited

U.S. PATENT DOCUMENTS

| | | | |
|---|---|---|---|
| 5,782,914 A | 7/1998 | Schankereli | |
| 5,824,703 A | 10/1998 | Clark, Jr. | |
| 5,957,919 A | 9/1999 | Laufer | |
| 5,964,752 A | 10/1999 | Stone | |
| 5,986,662 A | 11/1999 | Argiro et al. | |
| 6,053,909 A | 4/2000 | Shadduck | |
| 6,083,255 A | 7/2000 | Laufer et al. | |
| 6,102,037 A * | 8/2000 | Koch | 128/203.26 |
| 6,130,671 A | 10/2000 | Argiro | |
| 6,139,571 A * | 10/2000 | Fuller et al. | 607/105 |
| 6,162,232 A | 12/2000 | Shadduck | |
| 6,200,333 B1 | 3/2001 | Laufer | |
| 6,210,404 B1 | 4/2001 | Shadduck | |
| 6,219,059 B1 | 4/2001 | Argiro | |
| 6,283,989 B1 | 9/2001 | Laufer et al. | |
| 6,299,633 B1 | 10/2001 | Laufer | |
| 6,312,474 B1 | 11/2001 | Francis et al. | |
| 6,327,505 B1 | 12/2001 | Medhkour et al. | |
| 6,398,775 B1 | 6/2002 | Perkins et al. | |
| 6,409,723 B1 | 6/2002 | Edwards | |
| 6,468,313 B1 | 10/2002 | Claeson et al. | |
| 6,488,673 B1 | 12/2002 | Laufer et al. | |
| 6,493,589 B1 | 12/2002 | Medhkour et al. | |
| 6,508,816 B2 | 1/2003 | Shadduck | |
| 6,527,761 B1 | 3/2003 | Soltesz et al. | |
| 6,585,639 B1 * | 7/2003 | Kotmel et al. | 600/116 |
| 6,592,594 B2 | 7/2003 | Rimbaugh et al. | |
| 6,599,311 B1 | 7/2003 | Biggs et al. | |
| 6,610,043 B1 | 8/2003 | Ingenito | |
| 6,652,594 B2 | 11/2003 | Francis et al. | |
| 6,653,525 B2 | 11/2003 | Ingenito et al. | |
| 6,669,694 B2 | 12/2003 | Shadduck | |
| 6,679,264 B1 | 1/2004 | Deem et al. | |
| 6,682,520 B2 | 1/2004 | Ingenito | |
| 6,692,494 B1 | 2/2004 | Cooper et al. | |
| 6,712,812 B2 | 3/2004 | Roschak et al. | |
| 6,755,794 B2 | 6/2004 | Soukup | |
| 6,770,070 B1 * | 8/2004 | Balbierz | 606/41 |
| 6,776,765 B2 | 8/2004 | Soukup et al. | |
| 6,860,847 B2 | 3/2005 | Alferness et al. | |
| 6,901,927 B2 | 6/2005 | Deem et al. | |
| 6,904,909 B2 | 6/2005 | Andreas et al. | |
| 6,907,881 B2 | 6/2005 | Suki et al. | |
| 6,911,028 B2 | 6/2005 | Shadduck | |
| 7,022,088 B2 | 4/2006 | Keast et al. | |
| 7,031,504 B1 | 4/2006 | Argiro et al. | |
| 7,128,748 B2 | 10/2006 | Mooradian et al. | |
| 7,136,064 B2 | 11/2006 | Zuiderveld | |
| 7,144,402 B2 | 12/2006 | Kuester, III | |
| 7,144,588 B2 | 12/2006 | Oray et al. | |
| 7,192,400 B2 | 3/2007 | Campbell et al. | |
| 7,233,820 B2 | 6/2007 | Gilboa | |
| 2002/0077516 A1 * | 6/2002 | Flanigan | 585/241 |
| 2002/0111386 A1 * | 8/2002 | Sekins et al. | 514/759 |
| 2002/0177846 A1 | 11/2002 | Mulier et al. | |
| 2003/0181922 A1 | 9/2003 | Alferness | |
| 2004/0031494 A1 | 2/2004 | Danek et al. | |
| 2004/0038868 A1 | 2/2004 | Ingenito | |
| 2004/0047855 A1 | 3/2004 | Ingenito | |
| 2004/0055606 A1 | 3/2004 | Hendricksen et al. | |
| 2004/0068306 A1 | 4/2004 | Shadduck | |
| 2004/0199226 A1 | 10/2004 | Shadduck | |
| 2004/0244803 A1 * | 12/2004 | Tanaka | 128/207.16 |
| 2005/0016530 A1 | 1/2005 | McCutcheon et al. | |
| 2005/0166925 A1 | 8/2005 | Wilson et al. | |
| 2005/0171396 A1 | 8/2005 | Pankratov et al. | |
| 2005/0203483 A1 * | 9/2005 | Perkins et al. | 604/500 |
| 2005/0222485 A1 | 10/2005 | Shaw et al. | |
| 2006/0004400 A1 * | 1/2006 | McGurk et al. | 606/192 |
| 2006/0047291 A1 | 3/2006 | Barry | |
| 2006/0130830 A1 | 6/2006 | Barry | |
| 2006/0135955 A1 | 6/2006 | Shadduck | |
| 2006/0161233 A1 * | 7/2006 | Barry et al. | 607/113 |
| 2006/0162731 A1 | 7/2006 | Wondka et al. | |
| 2006/0200076 A1 | 9/2006 | Gonzalez et al. | |
| 2006/0224154 A1 | 10/2006 | Shadduck et al. | |
| 2007/0032785 A1 | 2/2007 | Diederich et al. | |
| 2007/0036417 A1 | 2/2007 | Argiro et al. | |
| 2007/0068530 A1 * | 3/2007 | Pacey | 128/207.14 |
| 2007/0091087 A1 | 4/2007 | Zuiderveld | |
| 2007/0092864 A1 | 4/2007 | Reinhardt et al. | |
| 2007/0109299 A1 | 5/2007 | Peterson | |
| 2007/0137646 A1 | 6/2007 | Weinstein et al. | |
| 2008/0132826 A1 | 6/2008 | Shadduck et al. | |

FOREIGN PATENT DOCUMENTS

| | | |
|---|---|---|
| WO | WO 03/086498 A2 | 10/2003 |
| WO | WO 2005/025635 A2 | 3/2005 |
| WO | WO 2005/102175 A2 | 11/2005 |
| WO | WO 2006/003665 A2 | 1/2006 |
| WO | WO 2006/055695 A1 | 5/2006 |
| WO | WO 2006/080015 A2 | 8/2006 |

OTHER PUBLICATIONS

Fishman et al., A randomized trial comparing lung-volume-reduction surgery with medical therapy for severe emphysema, N. Engl J Med, vol. 348, No. 21, pp. 2059-2073, May 22, 2003.

Homasson, et al., "Bronchoscopic cryotherapy for airway strictures caused by tumors," Chest, vol. 90, No. 2, pp. 159-164, Aug. 1986.

Kang, Li, "Efficient optimal net surface detection for image segmentation—from theory to practice," M.Sc. Thesis, The University of Iowa, 2003.

Marasso, et al., "Cryosurgery in bronchoscopic treatment of tracheobronchial stenosis," Chest, vol. 103, No. 2, pp. 472-474, Feb. 1993.

Marasso, et al., "Radiofrequency resection of bronchial tumours in combination with cryotherapy: evaluation of a new technique," Thorax, vol. 53, pp. 106-109, 1998.

Mathur et al., Fiberoptic bronchoscopic cryotherapy in the management of tracheobronchial obstruction, Chest, vol. 110, No. 3, pp. 718-723, Sep. 1996.

Morice et al.; Endobrinchial argon plasma coagulation for treatment of hemotysis and neoplastic airway obstruction, CHEST, vol. 119, No. 3, pp. 781-787, Mar. 2001.

Moulding et al.; Preliminary studies for achieving transcervical oviduct occlusion by hot water or low-pressure steam; Advances in Planned Parenthood; vol. 12, No. 2; pp. 79-85; 1977.

Pracht, Adam, "VIDA takes new approach," Iowa City Press-Citizen, Sep. 12, 2005.

Quin, Jacquelyn, "Use of neodymium yttrium aluminum garnet laser in long-term palliation of airway obstruction," Connecticut Medicine, vol. 59, No. 7, pp. 407-412, Jul. 1995.

Sutedja, et al., "Bronchoscopic treatment of lung tumors," Elsevier, Lung Cancer, 11, pp. 1-17, 1994.

Tschirren, Juerg, "Segmentation, anatomical labeling, branchpoint matching, and quantitative analysis of human airway trees in volumetric CT images," Slides from Ph.D. defense, The University of Iowa, 2003.

Barry et al.; U.S. Appl. No. 11/598,383 entitled "High pressure and high temperature vapor catheters and systems," filed Nov. 13, 2006.

Tschirren et al.; "Intrathoracic airway trees: segmentation and airway morphology analysis from low-dose CT scans;" IEEE Trans. Med. Imaging; vol. 24, No. 12; pp. 1529-1539 (2002).

Barry et al.; U.S. Appl. No. 12/256,197 entitled "Determining patient-specific vapor treatment and delivery parameters," filed Oct. 22, 2008.

Barry et al.; U.S. Appl. No. 12/409,370 entitled "Determining patient-specific vapor treatment and delivery parameters," filed Mar. 23, 2009.

Becker, et al., "Lung volumes before and after lung volume reduction surgery" am J Respir crit care med; vol. 157,pp. 1593-1599; (1998) Oct. 28, 1997.

* cited by examiner

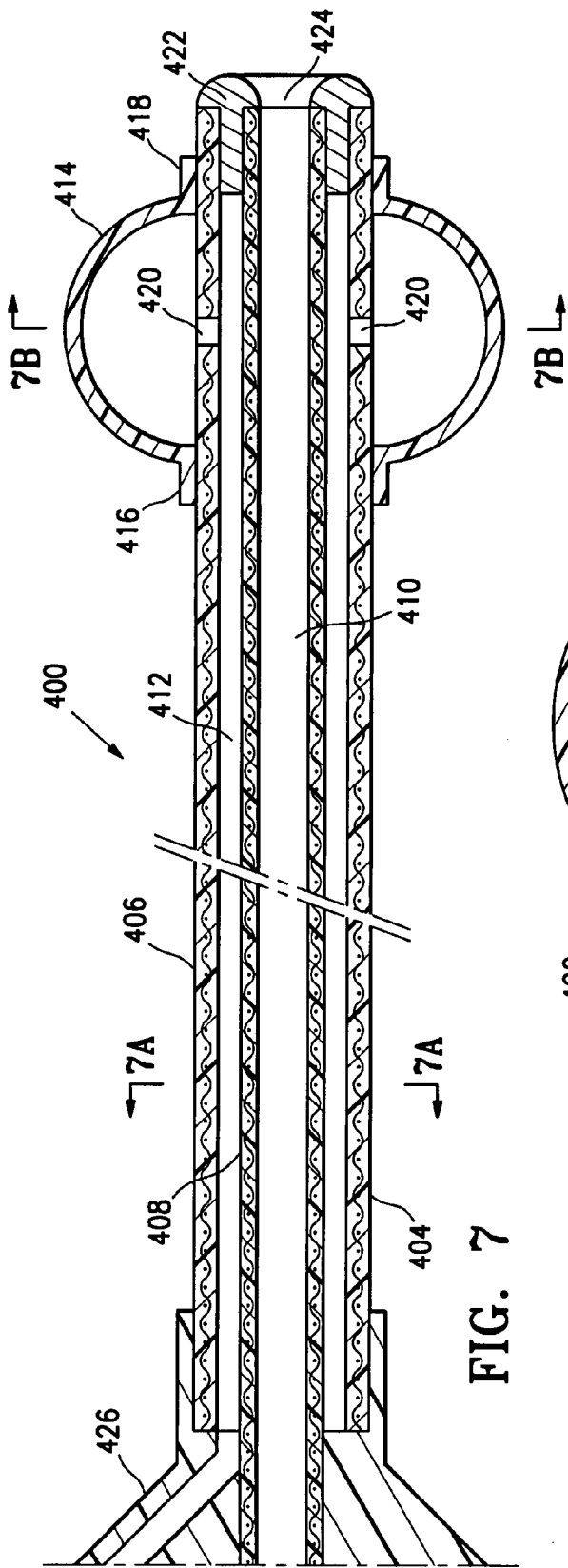
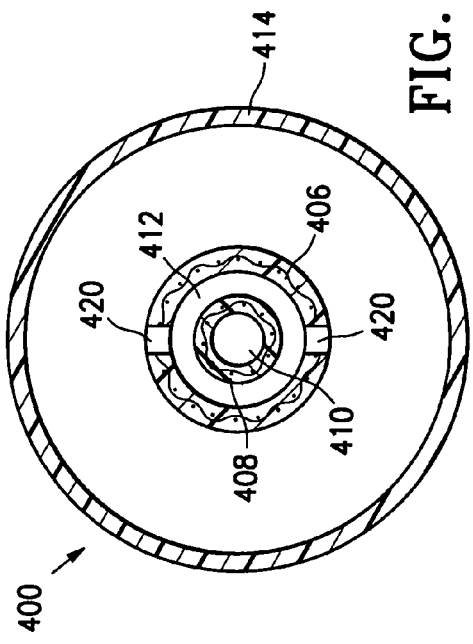
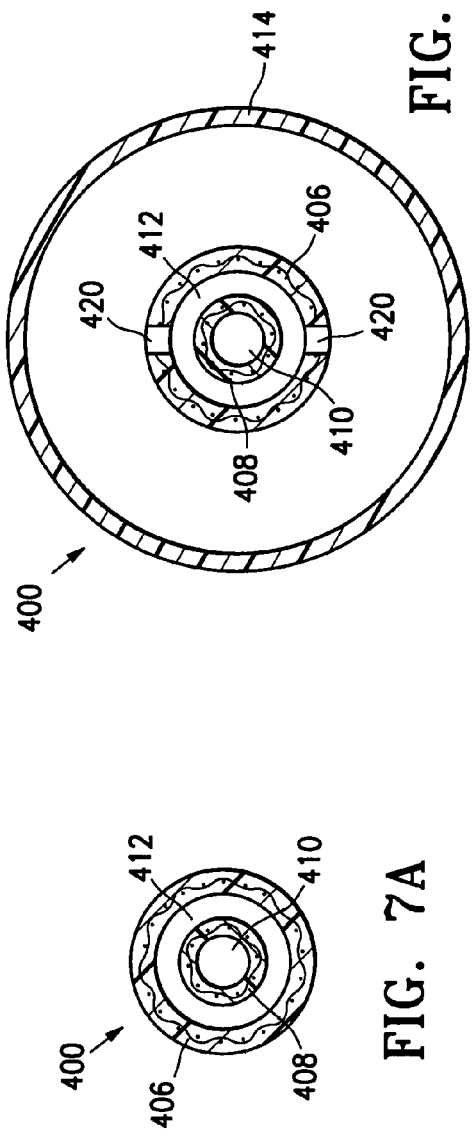
FIG. 7
FIG. 7A
FIG. 7B

US 8,585,645 B2

TREATMENT WITH HIGH TEMPERATURE VAPOR

RELATED APPLICATIONS

This application is related to application Ser. No. 11/598,383 concurrently filed Nov. 13, 2006, entitled HIGH PRESSURE AND HIGH TEMPERATURE VAPOR CATHETERS AND SYSTEMS, which is incorporated by reference herein in its entirety.

FIELD OF THE INVENTION

This invention relates to medical devices, systems and methods, and in particular to intrabronchial catheters, systems and methods for delivering a high pressure, high temperature vapor to one or more tissue targets in a patient's lungs.

BACKGROUND OF THE INVENTION

Heating therapies are increasingly used in various medical disciplines including cardiology, dermatology, orthopedics, oncology as well as a number of other medical specialties. In general, the manifold clinical effects of superphysiological tissue temperatures results from underlying molecular and cellular responses, including expression of heat-shock proteins, cell death, protein denaturation, tissue coagulation and ablation. Associated with these heat-induced cellular alternations and responses are dramatic changes in tissue structure, function and properties that can be exploited for a desired therapeutic outcome such as tissue injury, shrinkage, modification, destruction and/or removal.

Heating techniques in the lung pose several technical challenges because lung tissue is more aerated than most tissues and also due to its vascularization. Accordingly, these new heating methods, devices and systems for rapid, controllable, effective and efficient heating of lung tissue are needed. The present invention is directed at meeting these as well as other needs.

SUMMARY OF THE INVENTION

The present invention relates to novel methods for treating an intraluminal location by volumetricly heating one or more target tissues and particularly tissue in a patient's lungs. Preferably, the one or more target tissues are heated to superphysiological temperatures (temperatures above at least 45° C.) by dispersing a high temperature vapor into an airway (e.g. intrabronchial location) that ventilates the one or more target tissues. Because of the physiological characteristics of the airways, the vapor can be delivered focally or regionally dependant largely on where in the airways the vapor is dispersed. The target tissue is heated without causing pneumothorax.

In a first aspect of the invention, a method of treating a patient's lungs comprises providing an elongated device such as a catheter which has an inner lumen formed of heat resistant materials and configured to deliver heated vapor to a port in a distal portion of the catheter; advancing the catheter within the patient to a desired location therein, such as a lung; and delivering heated vapor through the inner lumen. Preferably, catheter has an inflatable member on a distal portion of the catheter and the inflatable member is inflated before heated vapor is delivered through the inner lumen to prevent proximal flow of the heated vapor.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 7 is a longitudinal cross-sectional view of yet another embodiment of a catheter in accordance with the present invention;

FIG. 7A transverse a cross-sectional view of the catheter of FIG. 7 taken along lines 7A-7A; and FIG. 7B is a transverse cross-sectional view of catheter illustrated in FIG. 7 taken along lines 7B-7B.

DETAILED DESCRIPTION OF THE INVENTION

Figure 1:
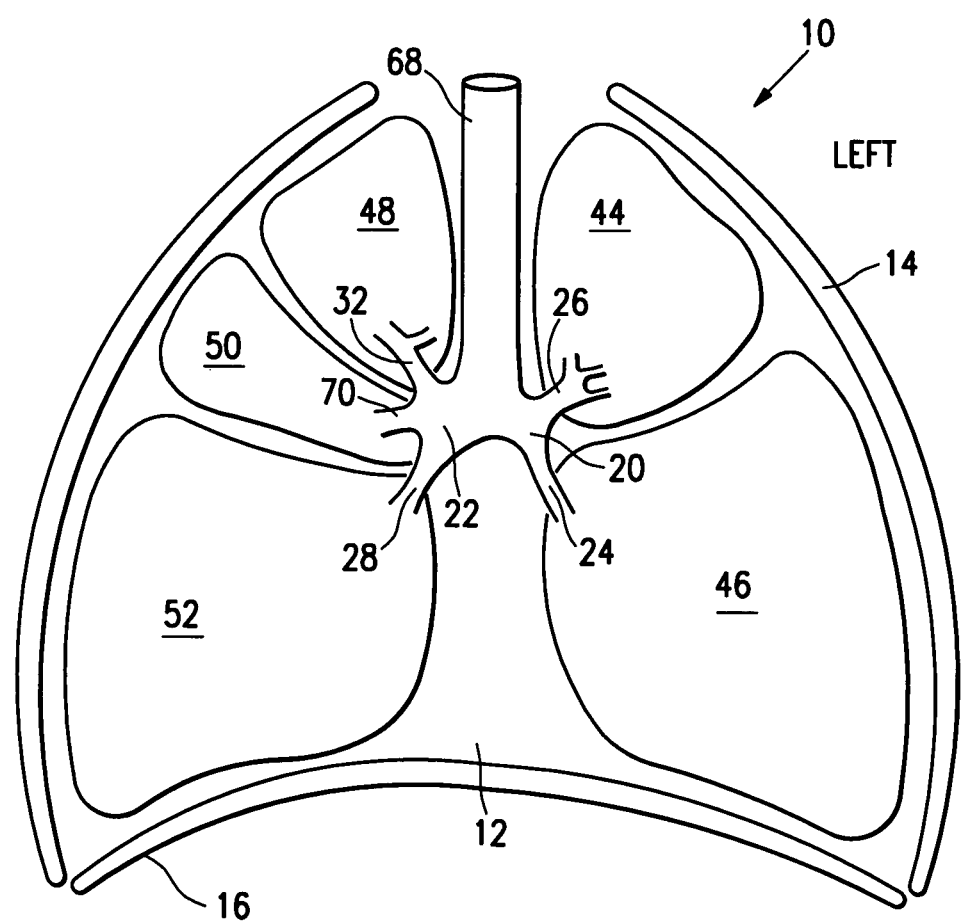
FIG. 1 illustrates a human respiratory system.

FIG. 1 illustrates a human respiratory system 10. The respiratory system 10 resides within the thorax 12 that occupies a space defined by the chest wall 14 and the diaphragm 16. The human respiratory system 10 includes left lung lobes 44 and 46 and right lung lobes 48, 50, and 52.

The respiratory system 10 further includes trachea 18; left and right main stem bronchus 20 and 22 (primary, or first generation) and lobar bronchial branches 24, 26, 28, 30, and 32 (second generation). Segmental and sub-segmental branches further bifurcate off the lobar bronchial branches (third and fourth generation). Each bronchial branch and sub-branch communicates with a different portion of a lung lobe, either the entire lung lobe or a portion thereof. As used herein, the term "air passageway" or "airway" means a bronchial branch of any generation, including the bronchioles and terminal bronchioles.

Figure 2:
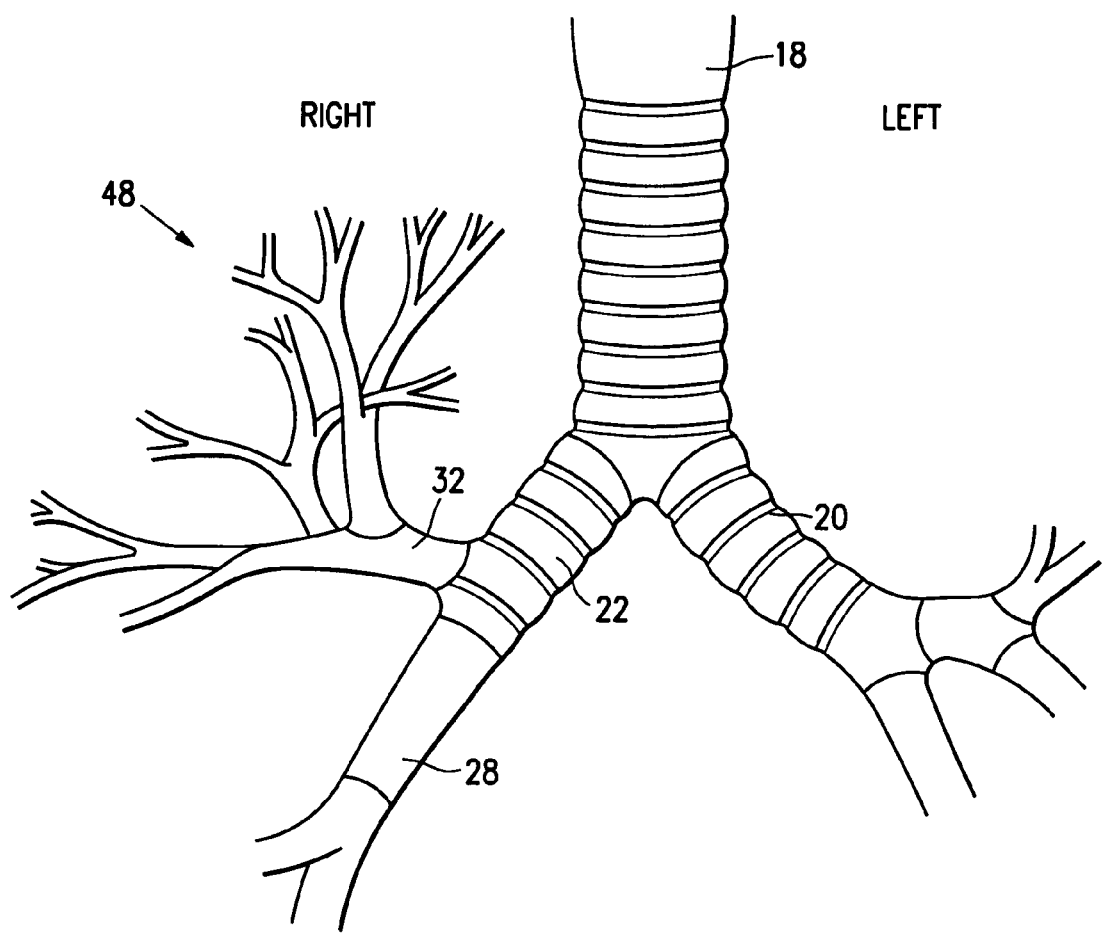
FIG. 2 illustrates the airway in the respiratory system.

FIG. 2 is a perspective view of the airway anatomy emphasizing the upper right lung lobe 48. In addition to the bronchial branches illustrated in FIG. 1, FIG. 2 shows sub-segmental bronchial branches (fourth generation) that provide air circulation (i.e. ventilation) to superior right lung lobe 48. The bronchial segments branch into six generations and the bronchioles branch into approximately another three to eight generations or orders. Each airway generation has a smaller diameter than its predecessor, with the inside diameter of a generation varying depending on the particular bronchial branch, and further varying between individuals. A typical lobar bronchus providing air circulation to the upper right upper lobe 48 has an internal diameter of approximately 1 cm.

Typical segmental bronchi have internal diameter of approximately of about 4 to about 7 mm.

The airways of the lungs branch much like the roots of a tree and anatomically constitute an extensive network of air flow conduits that reach all lung areas and tissues. The airways have extensive branching that distally communicates with the parenchyma alveoli where gas exchange occurs. Because of these physiological characteristics of the airways, a medium, such as a vapor, delivered through an airway can be delivered focally or more regionally depending largely on the airway location at which the medium is delivered or dispersed.

While not illustrated, a clear, thin, shiny covering, known as the serous coat or pleura, covers the lungs. The inner, visceral layer of the pleura is attached to the lungs and the outer parietal layer is attached to the chest wall 14. Both layers are held in place by a film of pleural fluid in a manner similar to two glass microscope slides that are wet and stuck together. Essentially, the pleural membrane around each lung forms a continuous sac that encloses the lung and also forms a lining for the thoracic cavity 12. The space between the pleural membranes forming the lining of the thoracic cavity 12 and the pleural membranes enclosing the lungs is referred to as the pleural cavity. If the air tight seal around the lungs created by the pleural members are breached (via a puncture, tear, or is otherwise damaged) air can enter the sac and cause the lungs to collapse.

Figure 3:
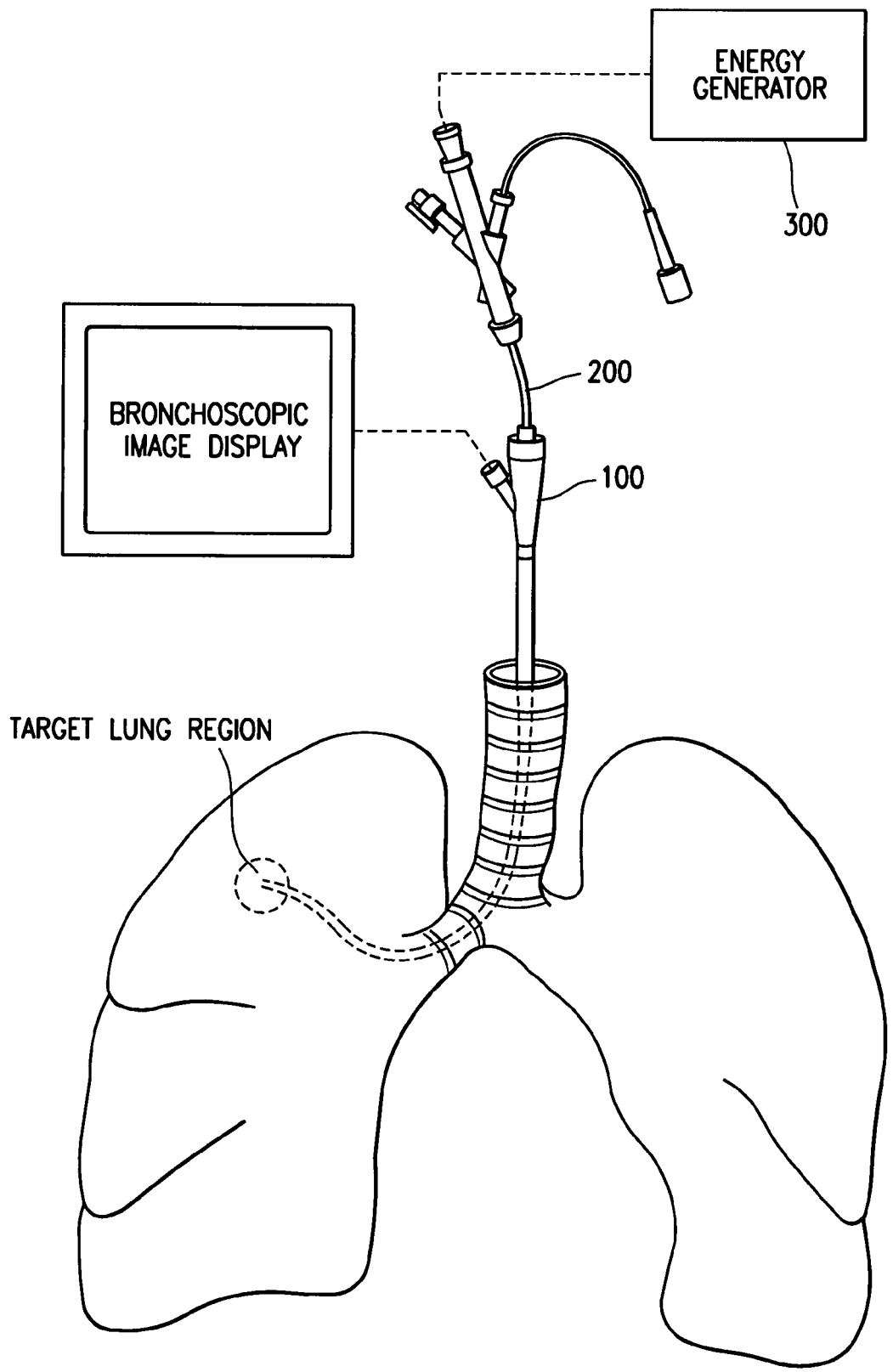
FIG. 3 illustrates one method of treating a volume of lung tissue in accordance with the present invention.

FIG. 3 illustrates generally a procedure in accordance with the present invention. FIG. 3 shows a bronchoscope 100 having a working channel into which an energy delivery catheter 200 is inserted. Bronchoscope 100 is inserted into a patient's lungs while the proximal portion of the energy delivery catheter 200 remaining outside of the patient. Energy delivery catheter 200 is adapted to operatively couple to an energy generator 300 as further discussed below.

Though not illustrated, patients can be intubated with a double-lumen endobronchial tube during the procedure, which allows for selective ventilation or deflation of the right and left lung. Depending on the location or locations of the target lung tissues to be treated, it may be preferable to stop ventilation of the target lung tissue. Also, while not illustrated, in an alternative embodiment, the procedure can be performed minimally invasively with energy catheter 200 introduced percutaneously through the chest wall and advanced to an appropriate location for with the aid of an introducer or guide sheath (with or without introduction into an airway).

Figure 4:
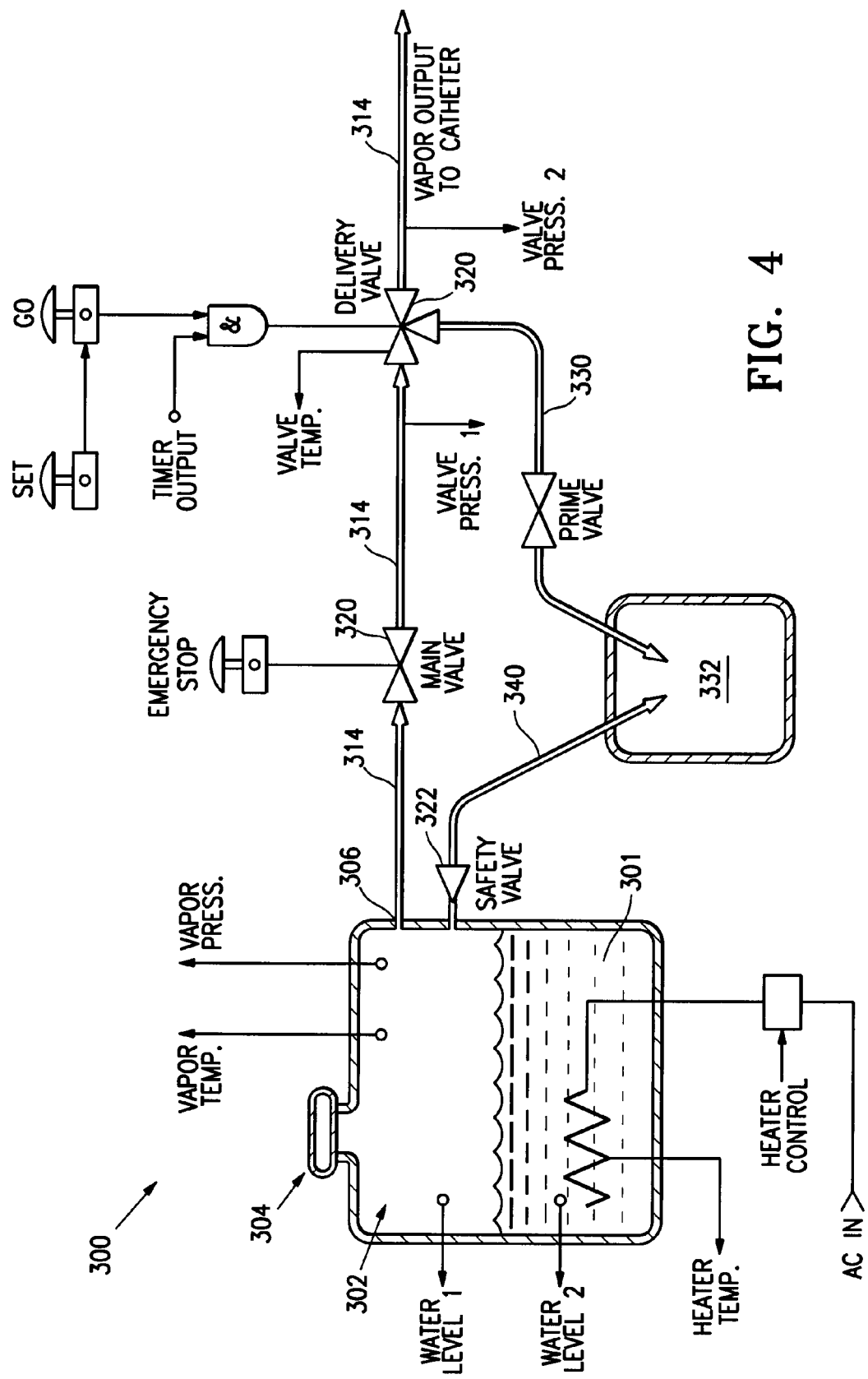
FIG. 4 is a schematic illustrating one embodiment of a vapor generator in accordance with the present invention.

FIG. 4 is a schematic diagram of one embodiment of the present invention wherein energy generator 300 is configured as a vapor generator. Preferably, vapor generator is configured to deliver a controlled dose of vapor to one or more target lung tissues. Generally, vapor generator 300 is adapted to convert a biocompatible liquid 301 (e.g. saline, sterile water or other biocompatible liquid), into a wet or dry vapor, which is then delivered to one or more target tissues. A wet vapor refers to a vapor that contains vaporous forms of the liquid as well as a non-negligible proportion of minute liquid droplets carried over with and held in suspension in the vapor. A dry vapor refers to a vapor contained little or no liquid droplets. In general, vapor generator 300 is configured to have a liquid capacity between about 1000 to 2500 cc and configured to generate a vapor having a pressure between about 5-50 psig and temperatures between about 100-175° C.

Vapor generator 300 is preferably configured as a self-contained, medical-grade generator unit comprising at least a controller (not shown), a vaporizing unit 302, a vapor inlet 304, a vapor outlet 306 and a connective handle (not shown).

The vaporizing unit 302 comprises a fluid chamber for containing a fluid 302, preferably a biocompatible, sterile fluid, in a liquid state. Vapor outlet 304 is coupled to one or more pipes or tubes 310, which in turn are in fluid communication with a vapor lumen of a hub assembly or other adapter, which in turn is adapted to operatively couple to the proximal end of energy delivery catheter 200, several embodiments of which are further described below. Vapor flow from vapor generator 300 to a catheter (and specifically a vapor lumen of said catheter) is depicted as a vapor flow circuit 314 wherein flow of the vapor in circuit 314 is indicated by arrows 314 in FIG. 4.

Vaporizer unit 302 is configured to heat and vaporize a liquid contained in a fluid chamber (not shown). Other components can be incorporated into the biocompatible liquid 301 or mixed into the vapor. For example, these components can be used in order to control perioperative and/or post procedural pain, enhance tissue fibrosis, and/or control infection. Other constituents, for the purpose of regulating vapor temperatures and thus control extent and speed of tissue heating, can be incorporated; for example, in one implementation, carbon dioxide, helium, other noble gases can be mixed with the vapor to decrease vapor temperatures.

Vaporizing unit 302 further comprises a fluid inlet 304 that is provided to allow liquid 301 to be added to the fluid chamber as needed. Fluid chamber can be configured to accommodate or vaporize sufficient liquid as need to apply vapor to one or more target tissues. Liquid in vaporizing unit 302 is heated and vaporized and the vapor flows into vapor outlet 304. A number of hollow thermally conductive pipes 314 are adapted to fluidly connect vapor outlet 304 and handle, which in turn is adapted to operatively couple to a variety of energy delivery catheters, which are further described below. Preferably, there is little or no vapor-to-liquid transition during movement of the vapor through vapor flow circuit 314. Vapor flow through vapor flow circuit 314 is unidirectional (in the direction of arrows 314). Accordingly one or more isolation valves 320 are incorporated in vapor flow circuit 314. Isolation valves 320, which are normally open during use of generator 300, minimize vapor flow in a direction opposite that of the vapor flow circuit 314.

A priming line 330, branching from main vapor flow circuit 314, is provided to minimize or prevent undesirable liquid-state water formation during vapor flow through vapor flow circuit 314. Pressure and temperature changes along vapor flow circuit 314 can affect whether the vapor is sustainable in a vapor state or condensed back into a liquid. Priming line 330 is provided to equalize temperatures and/or pressures along vapor flow circuit 314 in order to minimize or prevent undesirable liquid-state transition of the vapor during its progression through vapor flow circuit 314. In one embodiment, an initial "purge" or "priming" procedure can be preformed prior to delivery of a therapeutic vapor dose in order to preheat flow, circuit 314 thus maintaining a constant temperature and pressure in the main vapor flow circuit 314 prior to delivery of a vapor to the target lung tissue.

As shown in FIG. 4, priming line 330 terminates at evaporator 332, which is adapted to either house undesirable liquid in a collection unit (not shown) located within generator 300. In one embodiment, collection unit is adapted to house the liquid until a user or clinician is able to empty said collection unit. Alternatively, evaporator 332 is configured to evaporate and expel said undesirable liquid into the ambient air. Baffle plates (not shown) or other like means can be incorporated in evaporator 332 to facilitate maximal vapor-to-liquid transition. It should be understood that other suitable evaporator configurations could be included to facilitate vapor-to-liquid transition during a priming procedure of lines 314.

A number of sensors, operatively connected to a controller, can be incorporated into vapor generator 300. For example, in the liquid chamber, or along any point in vapor flow circuit 314, a number of sensors can be provided. Water level sensors, adapted to monitor the water level in the liquid chamber, can be included. These water level sensors are configured as upper and lower security sensors to sense or indicate when a liquid level in the fluid chamber is below or above a set fluid level. In example, if a water level in the fluid chamber falls below the level of a lower water control sensor, the controller can be configured to interrupt the operation of the vapor generator 300.

In yet another embodiment, pressure sensors, or manometers, can be included in vaporizing unit 302, or at various points along the vapor flow circuit 314, to measure the liquid or vapor pressures at various discrete locations and/or to measure vapor pressures within a defined segment along circuit 314. One or more control valves 320 can also be installed at various points in the vapor flow circuit 314 to control vapor flow for instance to control or increase the vapor flow or vapor flow rates in vapor flow circuit 314. In yet another embodiment, a safety valve 322 can be incorporated into the liquid chamber of vaporizing unit 302 and coupled to a vapor overflow line 340 if the need for removing or venting vaporizing unit 302 arises during generator 300 operation.

Figure 5:
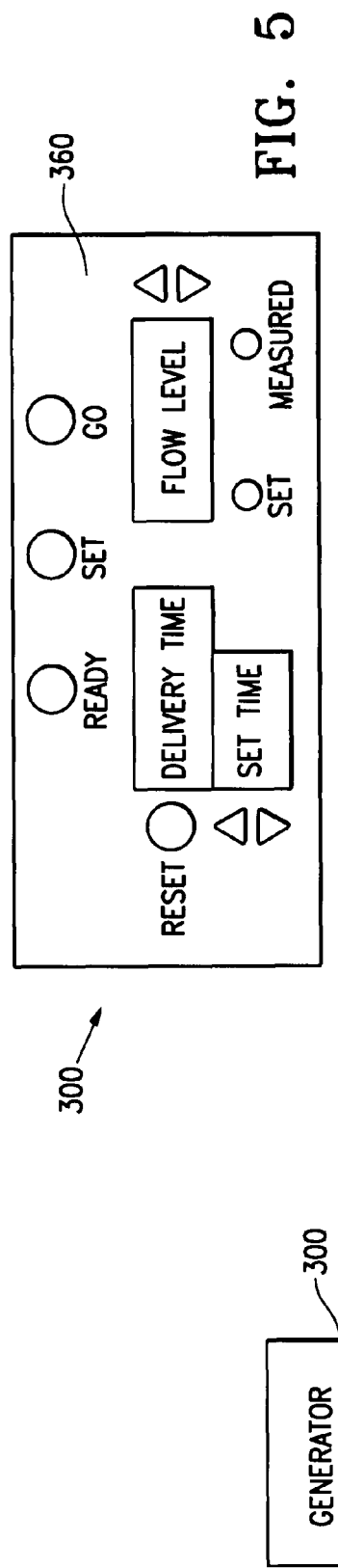
FIG. 5 illustrates one embodiment of a generator display or user interface.

FIG. 5 illustrates one embodiment of a user interface 360 of vapor generator 300. As illustrated, the user interface 360 comprises various visual readouts intended to provide clinical users information about various treatment parameters of interest, such as pressure, temperature and/or duration of vapor delivery. Vapor generator 300 can also be adapted to incorporate one or more auditory alerts, in addition or in lieu of, visual indicators provided on user interface 360. These one or more auditory alerts are designed to provide an alert to a clinical user, such as when vapor delivery is complete, when liquid chamber must be refilled or the like. As will be recognized by those in the art, other components, while not shown, can be incorporated including any of the following: a keyboard; a real-time imaging system display (such as a CT, fluoroscopy, ultrasound); memory system; and/or one or more recording systems.

Figure 6:
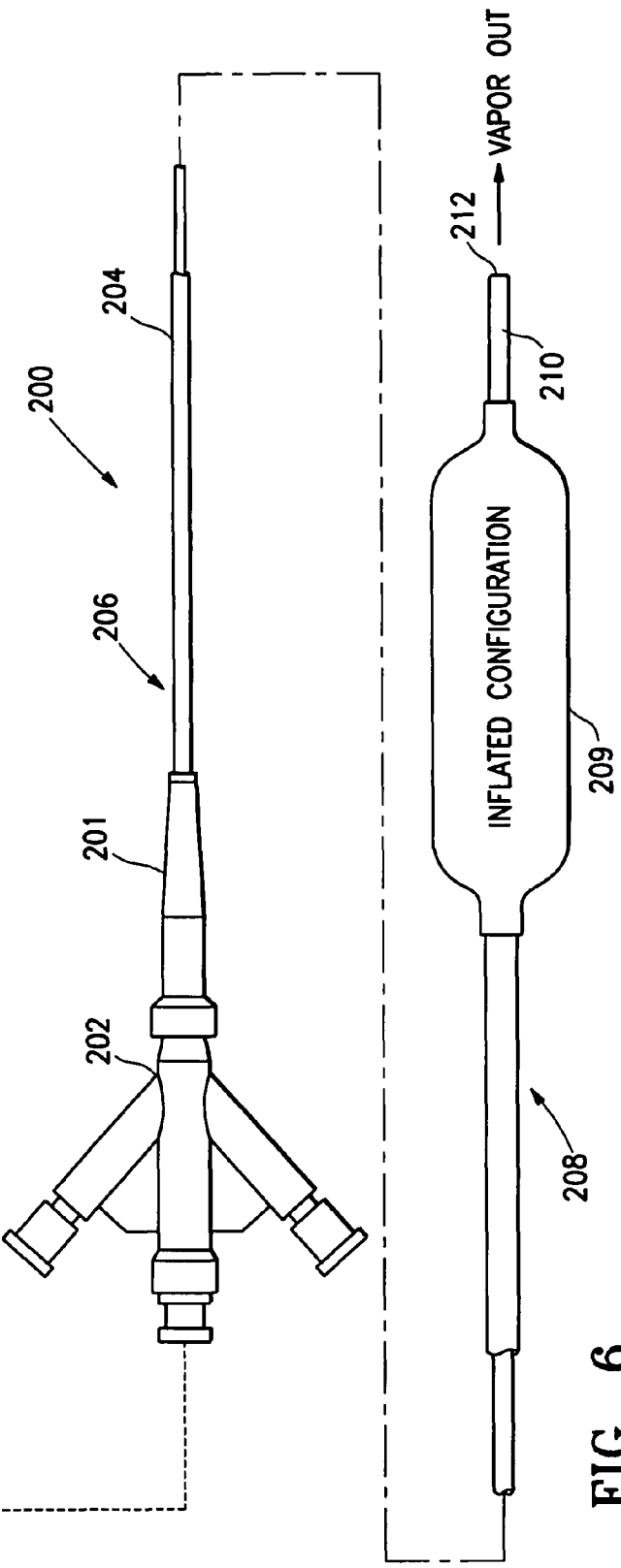
FIG. 6 is a perspective view of one embodiment of an energy delivery catheter in accordance with present invention.

FIG. 6 illustrates yet another aspect of the invention, in particular a vapor catheter 200 embodying various features of the present invention. Generally, catheter 200 is adapted to operatively connect to a control handle of vapor generator 300 via hub assembly 202. Catheter 200 includes elongate shaft 204 defined by proximal section 206 and distal section 208. Elongated shaft 204 is formed with at least one lumen (such as a vapor, inflation, sensing, imaging, guide wire, vacuum lumen) extending from proximal section 206 to distal section 208 of shaft 204. Starting at proximal section 206, catheter 200 comprises strain relief member 201.

Elongated shaft 204 further comprises at least one occlusive member 210 disposed at distal section 208 and distal tip 210 having at least one distal port 212. In one embodiment, the at least one distal port 212 is configured as a vapor outlet port. In yet another embodiment, vapor outlet port may also be used as an aspiration port while catheter is coupled to a vacuum source (not shown) in order to aspirate mucus, fluids, and other debris from an airway through which catheter 200 is advanced prior to vapor delivery. Alternatively, catheter 200 can be configured to include a separate vacuum lumen and aspiration ports as needed. Distal tip 210 can be adapted into a variety of shapes depending on the specific clinical need and application. For example, distal tip 210 can be adapted to be atraumatic in order to minimize airway damage during delivery.

The dimensions of the catheter are determined largely by the size airway lumen through which the catheter must pass in order to deliver the catheter to an airway location appropriate for treatment of the one or more target tissues. An airway location appropriate for treatment of a target lung tissue depends on the volume of the target tissue and the proximity of catheter tip to the target tissue. Generally, catheter 200 is low profile to facilitate placement of catheter distal tip 210 as close as practicable to proximally and peripherally located target lung tissue, i.e. in order to facilitate the catheter's advancement into smaller and deeper airways. In addition, the low profile feature of catheter 200 also ensures that catheter can be delivered to the lungs and airways through a working channel of a bronchoscope, including for example, through the working channels of ultra-thin bronchoscopes. Preferably, catheter 200 is slidably advanced and retracted from a bronchoscope working channel. The overall length and diameter of catheter 200 can be varied and adapted according to: the specific clinical application; size of the airway to be navigated; and/or the location of the one or more target tissues.

Occlusive member or members 210 are similarly configured to provide the smallest possible size when deflated to facilitate ready retraction of catheter 200 back into the working channel of a bronchoscope following completion of a treatment procedure involving delivery of one or more vapor doses to one or more target tissues. The one or more occlusive members 210 are provided to obstruct of proximal vapor flow and/or seat catheter 200 in the patient's airway during vapor delivery without slipping.

Obstruction of an airway by occlusive member 210 prevents retrograde flow of vapor to tissues located outside of the desired target tissues. Because of the physiological characteristics of the airways, in particular the fact that the airways ventilate and communicate specific lung parenchyma or tissues, vapor delivered or dispersed at a particular airway location (e.g. at the bronchial, sub segmental, main bronchi) determines whether there is a focal or regional heating of tissue. In addition to location of the catheter distal tip, other considerations that impact whether there is focal or regional tissue heating patterns (i.e. volume of tissue heated or size of thermal lesion) created include: time or duration of vapor delivery; the vapor flow rate; and vapor content (dry vs. wet; vapor alone vs. vapor cocktail). Preferably, the one or more occlusive members 210 are compliant to ensure: adequate seating; airway obstruction; and/or complete collapse following deflation.

Catheter 200 can be fabricated from a variety of suitable materials and formed by any process such as extrusion, blow molding, or other methods well know in the art. In general, catheter 200 and its various components are fabricated from materials that are relatively flexible (for advancement into tortuous airways) yet having good pushability characteristics and durable enough to withstanding the high temperatures and pressures of the vapor delivered using catheter 200.

Catheter 200 and elongated shaft 204 can be a tubular braided polyimide, silicone, or reinforced silicone. These materials are relatively flexible, yet have good pushability characteristics, while able to withstand the high temperature and pressures of vapor flow. Suitable materials should be adapted to withstand vapor pressures of up to 80 psig, at temperatures up to 170° C. Specific suitable materials include, for example, various braided polyimide tubing available, for example, from IW High Performance Conductors, Inc. Similarly, the one or more occlusive members 210 are preferably fabricated from similar materials having pressure and temperature tolerant attributes as elongated shaft 204, but preferably which is also compliant, such as silicone available from Dow Corning Q74720. As an added feature, catheter 200 and elongated shaft 204 can further be adapted to include varying flexibility and stiffness characteristics along the length of shaft 204 based on the clinical requirements and desired advantages. While not shown, various sensing members, including for example pressure, temperature and flow sensors known in the art can be incorporated into catheter 200. For example, catheter 200 can be adapted to include a sensing lumen for advancement or connection with various sensory devices such as pressure, temperature and flow sensors.

Turing now to FIG. 7, illustrated is a preferred embodiment of a vapor catheter 400. FIG. 7 is a longitudinal cross sectional view of the elongate shaft 404 while FIGS. 7A and 7B show transverse cross sectional views of the elongate shaft 404 taken along the lines 7A-7A and lines 7B-7B respectively.

In this preferred embodiment, catheter 400 comprises an elongated catheter shaft 404 having an outer tubular member 406 and an inner tubular member 408 disposed within outer tubular member 406. Inner tubular member 408 defines a vapor lumen 410 adapted to receive a vapor and which is in fluid communication with a vapor flow circuit 314 of generator 300. The coaxial relationship between outer tubular member 406 and inner tubular member 408 defines annular inflation lumen 412. Vapor lumen 410 terminates at vapor port 424.

Inflation balloon 414 is disposed on a distal section of elongated catheter shaft 404 and having proximal 416 and distal 418 balloon ends sealingly secured to outer tubular member 406. One or more inflation ports 420 are disposed on outer tubular member 406 between the proximal 416 and distal 418 ends of inflation balloon 414 so that the interior of inflation balloon 414 is in fluid communication with inflation lumen 412. (See FIG. 7B.)

As shown in FIG. 7, structural members 422 are disposed between inner tubular member 408 and outer tubular member 406 at distal vapor port 424 to seal inflation lumen 412 and provide structural integrity at the catheter tip. Structural members 422 are preferably made of stainless steel, nickel titanium alloys, gold, gold plated materials or other radiopaque materials, to provide catheter tip visibility under fluoroscopy and/or provide sufficient echogenicity so that the catheter tip is detectable using ultrasonography. Hub assembly 426 (or other adaptor) at the proximal end of catheter 400 is configured to direct an inflation fluid (such as a liquid or air) into inflation lumen 412 as well as provide access to vapor lumen 410.

FIG. 7B illustrates inflation balloon 414 in an inflated or expanded configuration. Inflation balloon 414 inflates to a cylindrical cross section equal to that of a target airway in order to obstruct the airway and prevent proximal or retrograde vapor flow. This inflated configuration is achieved at an inflation pressure within the working pressure range of balloon 414. Inflation balloon 414 has a working length, which is sufficiently long to provide adequate seating in a target airway without slippage during or prior to vapor delivery.

Suitable dimensions for the vapor catheter 400 in accordance with the present invention include an outer tubular member 406 which has an outer diameter of about 0.05 to about 0.16 inches, usually about 0.065 inches and an inner diameter of about 0.04 to about 0.15 inches, usually about 0.059 inches. The wall thickness of outer tubular member 406 and inner tubular member 408 can vary from about 0.001 to about 0.005 inches, typically about 0.003 inches. The inner tubular member 408 typically has an outer diameter of about 0.04 to about 0.15 inches, usually about 0.054 inches and an inner diameter of about 0.03 to about 0.14 inches, usually about 0.048 inches.

The overall working length of catheter 400 may range from about 50 to about 150 cm, typically about 110 to about 120 cm. Preferably, inflation balloon 414 has a total length about 5 to about 20 mm; a working length of about 1 to about 18 mm, preferably about 4 to about 8 mm. Inflation balloon 414 has an inflated working outer diameter of about 4 to about 20 mm, preferably about 4 to about 8 mm within a working pressure range of inflation balloon 414. In preferred embodiment, outer tubular member 406 and inner tubular member 408 is braided polyimide tubular member from IWG High Performance Conductors. Specifically, the braided polyimide tubular member comprises braided stainless steel, with the braid comprising rectangular or round stainless steel wires. Preferably, the braided stainless steel has about 90 picks per inch. The individual stainless steel strands may be coated with heat resistant polyimide and then braided or otherwise formed into a tubular member or the stainless steel wires or strands may be braided or otherwise formed into a tubular product and the braided surfaces of the tubular product may be coated with a heat resistant polyimide.

As will be appreciated by those skilled in the art, the catheters and generators of the present invention can be used to heat one or more target lung tissue to treat a variety of lung diseases and conditions, including but not limited to: lung tumors, solitary pulmonary nodules, lung abscesses, tuberculosis, as well as a variety of other diseases and disorders. In one embodiment, a procedure for inducing lung volume reduction (as a treatment for emphysema) involves advancing catheter 400 into a segmental or sub-segmental airway and delivering a controlled vapor dose. As will be appreciated by those skilled in the art, the vapor carries most of the energy and heat required to convert liquid in vapor generator from a liquid into a vapor. Upon dispersion of the vapor into the airways, the vapor penetrates into the interstitial channels between the cells, and distributes thermal area over a relatively large volume of tissue, permitting tissue heating to be accomplished quickly, usually with a few seconds or minutes. Vapor heating of target lung tissue is intended to cause tissue injury, shrinkage and/or ablation, in order to cause volumetric reduction of one or more target lung tissues. Lung volume reduction is immediate and/or occurs over several weeks or months.

Depending on the extent of the volumetric reduction (complete or partial reduction of a lobe) desired, catheter 400 is navigated into one or more airways, preferably as into the segmental or sub-segmental airways and the vapor delivered into as many airway as need during a single procedure to effect the therapeutically optimal extent of lung volume reduction. In a preferred embodiment, a vapor generator configured to create a vapor having a vapor pressure between about 5-50 psig, at a temperature between about 100°-170° degrees C. within vapor generator 300 is employed. The vapor catheter is delivered into the sub-segmental airways that communicate with either the left and right upper lobes, and vapor delivered for a period of 1-20 seconds in each of these airways, to effect volumetric reduction of the left and right upper lobes. Preferably, energy deliver to a target lung tissue is achieved without attendant plural heating sufficient to cause damage to the pleura or a pneumothoraces.

As will be appreciated by one skilled in the art, various imaging techniques (in addition to or in lieu of conventional bronchoscopic imaging) can be employed before, during and after a vapor treatment procedure. Real time fluoroscopy can be used to confirm depth of catheter 400 inside a patient's lung as well as confirm position of catheter in a desired airway. In yet another embodiment, real-time CT guided electromagnetic navigational systems, such as the SuperDimension®/Bronchus system can be employed to accurately guide catheters of the present invention to the desired tissues targets, especially to get the catheters close to target tissues that are peripherally located. In one embodiment of the invention, the present invention can be adapted to work through a working channel of a locatable guide or guide catheter of the SuperDimension CT navigational system.

A medical kit for performing volumetric vapor heating of one or more target lung tissues which comprises a packaged, sterile liquid or liquid composition and a high temperature vapor delivery catheter. Other embodiments of said medical kits can comprise instructions of use, syringes, and the like.

The invention has been discussed in terms of certain embodiments. One of skill in the art, however, will recognize that various modifications may be made without departing from the scope of the invention. For example, numerous variations, changes, and substitutions will now occur to those skilled in the art without departing from the invention. Moreover, while certain features may be shown or discussed in relation to a particular embodiment, such individual features may be used on the various other embodiments of the invention. In addition, while not provided, other energy modalities can be employed for volumetric heating of target lung tissue and its understood that in conjunction with or instead of vapor, such as modalities such as RF, laser, microwave, cryogenic fluid, a resistive heating source, ultrasound and other energy delivery mechanisms can be employed for heating a target lung volume.

What is claimed is:

1. A method of heating target lung tissue within a patient, comprising:
   providing a catheter which has an inner lumen formed at least in part of heat resistant material and which is configured to deliver heated vapor to a port in a distal portion of the catheter;
   advancing the catheter within the patient; and
   delivering water vapor at a temperature between about 100° C. to about 175° C. from a vapor source external to the patient through the inner lumen of the catheter to the target lung tissue.

2. The method of claim 1 wherein the catheter has an inner tubular member formed at least in part of heat resistant material which defines at least in part the inner lumen.

3. The method of claim 2 wherein the heat resistant material is polyimide.

4. The method of claim 2 wherein the catheter has an outer tubular member which is formed of heat resistant material and which is disposed about the inner tubular member forming an inner lumen therebetween.

5. The method of claim 4 wherein the heat resistant material of the outer tubular member is polyimide.

6. The method of claim 1 wherein the catheter has an enlarged or enlargeable member on a distal portion of the catheter to prevent proximal flow of the heated vapor upon discharge from the catheter.

7. The method of claim 6 wherein the enlarged or enlargeable member is inflatable.

8. The method of claim 7 wherein the enlarged or enlargeable member is inflated before heated vapor is delivered through the inner lumen of the catheter.

9. The method of claim 7 wherein the enlarged or enlargeable member is formed of compliant polymeric material.

10. The method of claim 9 wherein the polymeric material is a silicone.

11. The method of claim 1 wherein the target lung tissue is heated to a temperature above 45° C.

12. The method of claim 1 further comprising volumetrically reducing the target lung tissue by heating the target lung tissue with the water vapor.

13. The method of claim 12 wherein the delivering step comprises delivering the vapor to the target lung tissue for a period of 1-20 seconds.

14. The method of claim 12 wherein the reducing step is performed without causing a pneumothorax.

15. A method of performing lung volume reduction to treat a lung disorder, the method comprising:
   providing a catheter which has an inner lumen formed at least in part of heat resistant material and which is configured to deliver heated vapor to a port in a distal portion of the catheter;
   advancing the catheter within the patient;
   delivering water vapor at a temperature between about 100° C. to about 175° C. to target lung tissue from a vapor source external to the patient through a heat resistant catheter; and
   volumetrically reducing the target lung tissue by heating the target lung tissue with the water vapor.

16. The method of claim 15 wherein the delivering step comprises delivering the vapor to the target lung tissue for a period of 1-20 seconds.

17. The method of claim 15 the volumetrically reducing step comprises heating the target lung tissue with the water vapor to a temperature above 45° C.

* * * * *